United States Patent [19]
Penn et al.

[11] Patent Number: 6,099,560
[45] Date of Patent: Aug. 8, 2000

[54] EXPANDABLE BIFURCATED STENT AND METHOD FOR DELIVERY OF SAME

[75] Inventors: Ian M. Penn; Donald R. Ricci, both of Vancouver, Canada

[73] Assignee: Divysio Solutions Ltd., Vancouver, Canada

[21] Appl. No.: 09/074,493

[22] Filed: May 8, 1998

Related U.S. Application Data

[63] Continuation of application No. 08/605,189, Feb. 28, 1996, Pat. No. 5,755,771.

[30] Foreign Application Priority Data

Nov. 3, 1997 [CA] Canada .................................. 2134997

[51] Int. Cl.⁷ ...................................................... A61F 2/06
[52] U.S. Cl. ........................................................ 623/1.35
[58] Field of Search .................................. 623/1, 1.35

[56] References Cited

U.S. PATENT DOCUMENTS

| | | | |
|---|---|---|---|
| 3,993,078 | 11/1976 | Bergentz et al. | 128/334 |
| 4,733,665 | 3/1988 | Palmaz | 128/343 |
| 4,739,762 | 4/1988 | Palmaz | 128/343 |
| 4,800,882 | 1/1989 | Gianturco | 128/343 |
| 4,994,071 | 2/1991 | MacGregor | 606/194 |
| 5,037,392 | 8/1991 | Hillstead | 604/96 |
| 5,102,417 | 4/1992 | Palmaz | 606/195 |
| 5,139,480 | 8/1992 | Hickle | 623/12 |
| 5,161,547 | 11/1992 | Tower | 128/898 |
| 5,197,978 | 3/1993 | Hess | 623/1 |
| 5,282,823 | 1/1994 | Schwartz et al. | 606/198 |
| 5,316,023 | 5/1994 | Palmaz et al. | 128/898 |
| 5,342,387 | 8/1994 | Summers | 606/198 |
| 5,395,390 | 3/1995 | Simon et al. | 606/198 |
| 5,421,955 | 6/1995 | Lau et al. | 216/48 |
| 5,443,500 | 8/1995 | Sigwart | 623/1 |
| 5,449,373 | 9/1995 | Pinchasik et al. | 606/198 |
| 5,458,615 | 10/1995 | Klemm et al. | 606/198 |
| 5,496,365 | 3/1996 | Sgro . | |
| 5,514,154 | 5/1996 | Lau et al. | 606/195 |
| 5,522,880 | 6/1996 | Barone et al. | 623/1 |
| 5,540,712 | 7/1996 | Kleshinski | 623/1 |
| 5,575,817 | 11/1996 | Martin | 623/1 |

(List continued on next page.)

FOREIGN PATENT DOCUMENTS

| | | | |
|---|---|---|---|
| 0566807 | 10/1993 | European Pat. Off. | A61F 2/06 |
| 0669114 | 8/1995 | European Pat. Off. | A61F 2/06 |
| 2678508 | 7/1991 | France | A61F 2/06 |
| WO9412136 | 9/1994 | WIPO | A61F 21/06 |
| WO9509584 | 4/1995 | WIPO | A61F 2/06 |
| WO9526695 | 10/1995 | WIPO | A61F 2/06 |
| WO 95/31945 | 2/1996 | WIPO | A61F 2/06 |
| WO 96/03092 | 2/1996 | WIPO | A61F 2/02 |
| WO 97/04721 | 2/1997 | WIPO | A61F 2/06 |

*Primary Examiner*—Michael J. Milano
*Attorney, Agent, or Firm*—Fitzpatrick, Cella, Harper & Scinto

[57] ABSTRACT

An expandable stent comprising a proximal end and a distal end in communication with one another, a tubular wall disposed between the proximal end and the distal end, the tubular wall having a longitudinal axis and a porous surface defined by a plurality intersecting members arranged to define a first repeating pattern which is a polygon having a pair of side walls substantially parallel to the longitudinal axis, a first concave-shaped wall and a second convex-shaped wall connecting the side walls, the first wall and the second wall being equidistant along an axis which is parallel to the longitudinal axis, the stent being expandable from a first, contracted position to a second, expanded position upon the application of a radially outward force on the interior of the stent. A particularly preferred form of the stent is an expandable bifurcated stent comprising a proximal end and a distal end in communication with one another, the proximal end comprising a primary passageway and the distal end comprising a pair of secondary passageways, the stent being expandable from a first, contracted position to a second, expanded position upon the application of a radially outward force on the stent. A method of delivering the bifurcated stent to a target body passageway is also provided.

1 Claim, 3 Drawing Sheets

U.S. PATENT DOCUMENTS

| | | | |
|---|---|---|---|
| 5,634,941 | 6/1997 | Winston | 623/12 |
| 5,643,312 | 7/1997 | Fischell et al. | 606/198 |
| 5,851,228 | 12/1998 | Pinheiro | 623/1.35 |
| 5,855,598 | 1/1999 | Pinchuk | 623/1.35 |
| 5,906,640 | 5/1999 | Penn | 623/1.35 |
| 5,916,263 | 6/1999 | Goicoechea | 623/1.35 |

EXPANDABLE BIFURCATED STENT AND METHOD FOR DELIVERY OF SAME

This application is a Continuation of U.S. application Ser. No. 08/605,189, filed Feb. 28, 1996 now U.S. Pat. No. 5,755,771.

TECHNICAL FIELD

The present invention relates to an expandable bifurcated stent and to a method for delivery of same.

BACKGROUND ART

Stents are generally known. Indeed, the term "stent" has been used interchangeably with terms such as "intraluminal vascular graft" and "expansible prosthesis". As used throughout this specification the term "stent" is intended to have a broad meaning and encompasses any expandable prosthetic device for implantation in a body passageway (e.g. a lumen or artery).

In the past six to eight years, the use of stents has attracted an increasing amount of attention due the potential of these devices to be used, in certain cases, as an alternative to surgery. Generally, a stent is used to obtain and maintain the patency of the body passageway while maintaining the integrity of the passageway. As used in this specification, the term "body passageway" is intended to have a broad meaning and encompasses any duct (e.g. natural or iatrogenic) within the human body and can include a member selected from the group comprising: blood vessels, respiratory ducts, gastrointestinal ducts and the like.

Initial stents were self-expanding, spring-like devices which were inserted in the body passageway in a contracted state. When released, the stent would automatically expand and increase to a final diameter dependent on the size of the stent and the elasticity of the body passageway. Such stents were known in the art as the Wallstent™.

The self-expanding stents were found by some investigators to be deficient since, when deployed, they could place undue, permanent stress on the walls of the body passageway. This led to the development of various stents which were controllably expandable at the target body passageway so that only sufficient force to maintain the patency of the body passageway was applied in expanding the stent.

Generally, in these later systems, a stent, in association with a balloon, is delivered to the target area of the body passageway by a catheter system. Once the stent has been properly located (the target area of the body passageway can be filled with a contrast medium to facilitate visualization during fluoroscopy), the balloon is expanded thereby expanding the stent so that the latter is urged in place against the body passageway. As indicated above, the amount of force applied is at least that necessary to maintain the patency of the body passageway. At this point, the balloon is deflated and withdrawn within the catheter, and subsequently removed. Ideally, the stent will remain in place and maintain the target area of the body passageway substantially free of blockage (or narrowing).

A stent which has gained some notoriety in the art is known as the Palmaz-Schatz™ Balloon Expandable Stent (hereinafter referred to as "the Palmaz-Schatz stent"). This stent is discussed in a number of patents including U.S. Pat. Nos. 4,733,665, 4,739,762, 5,102,417 and 5,316,023, the contents of each of which are hereby incorporated by reference.

Another stent which has gained some notoriety in the art is known as Gianturco-Roubin Flex-Stent™ (hereinafter referred to as "the Gianturco-Roubin stent"). This stent is discussed in a number of patents including U.S. Pat. Nos. 4,800,882, 4,907,336 and 5,041,126, the contents of each of which are hereby incorporated by reference.

Other types of stents are disclosed in the following patents:

U.S. Pat. No. 5,035,706 (Gianturco et al.),
U.S. Pat. No. 5,037,392 (Hillstead),
U.S. Pat. No. 5,147,385 (Beck et al.),
U.S. Pat. No. 5,282,824 (Gianturco),
Canadian patent 1,239,755 (Wallsten), and
Canadian patent 1,245,527 (Gianturco et al.), the contents of each of which are hereby incorporated by reference.

All of the stents described in the above-identified patents share the common design of being mono-tubular and thus, are best suited to be delivered and implanted in-line in the body passageway. These known stents are inappropriate for use in a bifurcated body passageway (e.g. a body passageway comprising a parent passageway that splits into a pair of passageways). Further, these stents are inappropriate for use in a body passageway having side branches since: (i) accurate placement of the stent substantially increases the risk to the patient, (ii) the risk of passageway closure in the side branches is increased, and (iii) the side branches will be substantially inaccessible.

Indeed the Physician Guide published in support of the Palmaz-Schatz stent states on page 32 (the contents of which are hereby incorporated by reference):

" . . . no attempt should be made following placement of a PALMAZ-SCHATZ stent to access the side branch with a guide wire or a balloon, as such attempts may result in additional damage to the target vessel or the stent. Attempts to treat obstructed side branches within stented segments can result in balloon entrapment, necessitating emergency bypass surgery."

Thus, when installed, the Palmaz-Schatz stent admittedly shields side branches emanating from the target area of the body passageway effectively permanently. This can be problematic since the only way to treat blockage or other problems associated with the side branches is to perform the type of surgery which installation of the stent was intended to avoid.

This contraindication for conventional mono-tubular stents is corroborated by a number of investigators. See, for example, the following:

1. *Interventional Cardiovascular Medicine: Principles and Practice* (1994); Publisher: Churchill Livingstone Inc.; pages 221–223 (Ohman et al.), 487–488 (Labinaz et al.), 667–668 (Bashore et al.) and 897 (Bailey et al.), including references cited therein;
2. Gianturco-Roubin Flex-Stent™ Coronary Stent: Physician's Guide; page 2, Paragraph 3 under WARNINGS;
3. *Circulation*, Vol. 83, No. 1, January 1991 (Schatz et al.); entitled "Clinical Experience With the Palmaz-Schatz Coronary Stent"; pages 148–161 at page 149; and
4. *American Heart Journal*, Vol. 127, No. 2, February 1994 (Eeckhout et al.); entitled "Complications and follow-up after intracoronary stenting: Critical analysis of a 6-year single-center experience"; pages 262–272 at page 263, the contents of each of which are hereby incorporated by reference.

Further, some investigators have attempted to install individual stents in each branch of the bifurcated body passageway. However, this approach is fraught with at least two significant problems. First, implantation of three individual stents, together with the expansive forces generated upon implantation results in subjecting the central walls of the bifurcated body passageway to undue stress which may lead to post-procedural complications. Second, since the central walls of the bifurcated body passageway are not supported by the individual stents, this area of the passageway is left substantially unprotected and susceptible to blockage.

One particular problem area with bifurcated body passageways is the occurrence of bifurcation lesions within the coronary circulation. Generally, these legions may be classified as follows:

| Type | Characteristic |
|---|---|
| A | Prebranch stenosis not involving the ostium of the side branch; |
| B | Postbranch stenosis of the parent vessel not involving the origin of the side branch; |
| C | Stenosis encompassing the side branch but not involving the ostium; |
| D | Stenosis involving the parent vessel and ostium of the side branch; |
| E | Stenosis involving the ostium of the side branch only; and |
| F | Stenosis discretely involving the parent vessel and ostium of the side branch. |

See *Atlas of Interventional Cardiology* (Popma et al.), 1994, pages 77–79, the contents of which are hereby incorporated by reference. The presence of bifurcation lesions is predictive of increased procedural complications including acute vessel closure.

Detailed classification of other bifurcated body passageways is relatively undeveloped given the lack of non-surgical treatment approaches.

Indeed, to the knowledge of the Applicant's, heretofore, a proven expandable bifurcated stent has been unavailable.

It would be desirable to have an expandable bifurcated stent since this would be useful in treating aneurysms, blockages and other ailments. It would also be desirable if such a stent was relatively easy to install.

DISCLOSURE OF THE INVENTION

It is an object of the present invention to provide a novel expandable stent which obviates or mitigates at least one of the above-mentioned disadvantages of the prior art.

It is another object of the present invention to provide a novel method for implanting an expandable stent.

Accordingly, in one of its aspects, the present invention provides an expandable bifurcated stent comprising a proximal end and a distal end in communication with one another, the proximal end comprising a primary passageway and the distal end comprising a pair of secondary passageways, the stent being expandable from a first, contracted position to a second, expanded position upon the application of a radially outward force exerted on the stent.

In another of its aspects, the present invention provides an expandable stent comprising a proximal end and a distal end in communication with one another, a tubular wall disposed between the proximal end and the distal end, the tubular wall having a longitudinal axis and a porous surface defined by a plurality of intersecting members arranged to define a first repeating pattern which is a polygon having a pair of side walls substantially parallel to the longitudinal axis, a first concave-shaped wall and a second convex-shaped wall connecting the side walls, the first wall and the second wall being equidistant along an axis which is parallel to the longitudinal axis, the stent being expandable from a first, contracted position to a second, expanded position upon the application of a radially outward force exerted on the stent.

In yet another of its aspects, the present invention provides a method for delivery to a target body passageway of an expandable bifurcated stent comprising a proximal end and a distal end in communication with one another, the proximal end comprising a primary passageway and the distal end comprising a pair of secondary passageways, the stent being expandable from a first, contracted position to a second, expanded position upon the application of a radially outward force exerted on the stent, the method comprising the steps of:

disposing the stent in the first, contracted position on a catheter;

inserting the stent and catheter within the target body passageway by catheterization of the target body passageway;

exerting a radially outward expansive force on the stent such that the stent assumes the second, expanded position and is urged against the target body passageway.

Thus, an aspect of the present invention relates to the provision of an expandable bifurcated stent. To the knowledge of the Applicant's, an expandable bifurcated stent has heretofore been unknown. As used throughout this specification, the term "bifurcated stent" is intended to have a broad meaning and encompasses any stent having a primary passageway to which is connected at least two secondary passageways. Thus, trifurcated stents are encompassed herein. Further, one of the secondary passageways can be a continuation of the primary passageway with the result that the other secondary passageway is essentially a side branch to the primary passageway.

The Applicant's have also discovered that the use of a specific repeating pattern in a porous stent is particularly advantageous. Generally, the repeating pattern is a polygon having a pair of side walls substantially parallel to the longitudinal axis of the stent passageway in question, a first concave-shaped wall and a second convex-shaped wall connecting the side walls, the first wall and the second wall being equidistant along an axis which is parallel to the longitudinal axis of the stent passageway in question. As used throughout this specification, the terms "concave-shaped" and "convex-shaped" are intended to have a broad meaning and a shape having apex. Thus, the apex can be the top of a smooth curve. Alternatively, the apex can be a point or top of a segmented line. The important point is that the apex of the concave-shaped wall is directed into the polygon whereas the apex of the convex-shaped wall is directed away from the polygon.

This repeating pattern is useful in both the novel bifurcated stent described herein and conventional mono-tubular stents. The advantages associated with the use of such a repeating pattern include the following:

1. The stent is controllably expandable;
2. The stent is flexible and thus, can be deliver via and/or implanted in curved body passageways; and
3. Access to side branches is maintained, unlike the Palmaz-Schatz stent described hereinabove.

The stent of the present invention (bifurcated or mono-tubular) can further comprise coating material thereon. The coating material can be one or more of a biologically inert material (i.e. to reduce the thrombogenicity of the stent), a medicinal composition which leaches in the wall of the body passageway after implantation (e.g. to provide anticoagulant action and the like).

BRIEF DESCRIPTION OF THE DRAWINGS

Embodiments of the present invention will be described with reference to the accompanying drawings wherein like numerals designate like parts and in which.

BEST MODE FOR CARRYING OUT THE INVENTION

Figure 1:
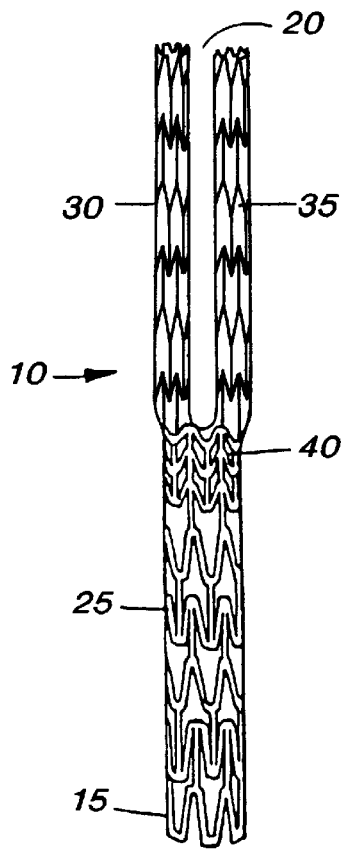
FIG. 1 illustrates a perspective view of a bifurcated stent in a first, contracted position.

With reference to FIG. 1, there is illustrated a stent 10. Stent 10 comprises a proximal end 15 and a distal end 20. Proximal end 15 comprises a primary passageway 25. Distal end 20 comprises a pair of secondary passageways 30,35. Secondary passageways 30,35 are connected to primary passageway 25 at an intersection point 40. As will be appreciated by those of skill in the art, the length of primary passageway 25 and secondary passageways 30,35 is not particularly restricted and is selected to optimize both deliverability of the stent (shorten) and vessel coverage (lengthen).

Figure 2:
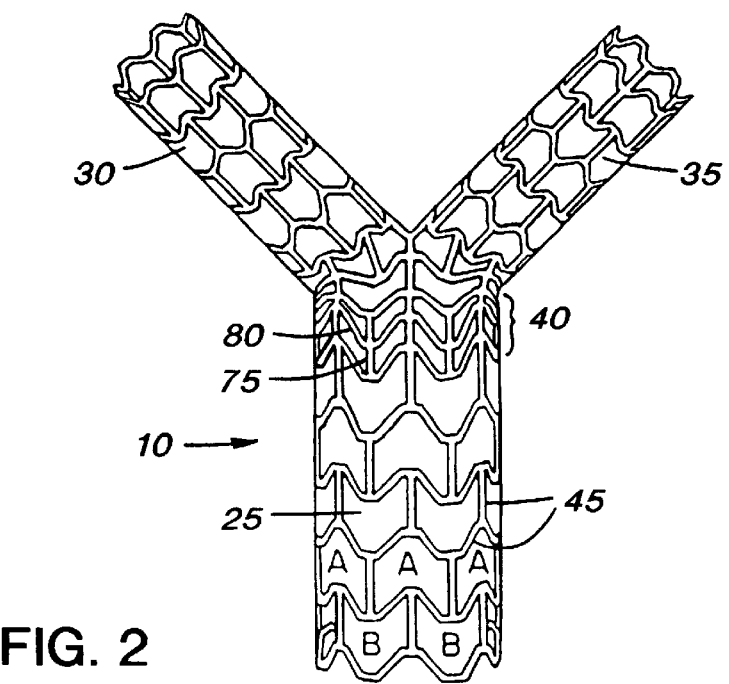
FIG. 2 illustrates an enlarged perspective view of the bifurcated stent of FIG. 1 in a second, expanded position.

With reference to FIG. 2, there is illustrated an enlarged perspective view of the bifurcated stent illustrated in FIG. 1 in a second, expanded position. As illustrated, secondary passageways 30,35 are split apart more than they are when the bifurcated stent is in the first, contracted position (FIG. 1).

As illustrated, primary passageway 25 and secondary passageways 30,35 are porous. The porosity of these passageways is defined by a plurality of intersecting members 45. Intersecting members 45 define a first repeating pattern designated A and a second repeating pattern designated B in FIG. 2. The nature of first repeating pattern A and second repeating pattern B will be discussed in more detail hereinbelow with reference to FIG. 4.

Figure 3:
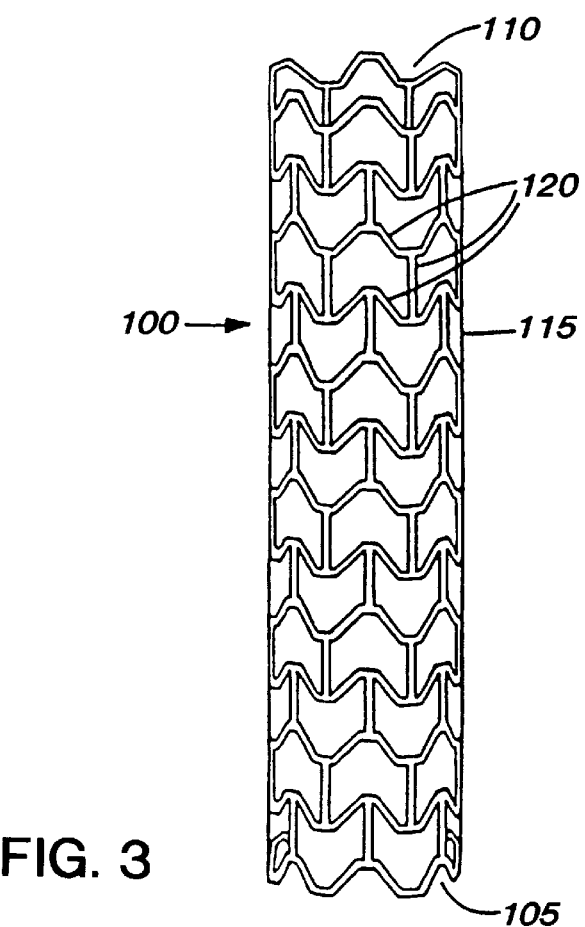
FIG. 3 illustrates a perspective view of a mono-tubular stent in a second, expanded position.

With reference to FIG. 3, there is illustrated a perspective view of a mono-tubular stent 100. Stent 100 comprises a proximal end 105 and a distal end 110. Disposed between proximal end 105 and distal end 110 is a tubular wall 115. Tubular wall 115 is porous. The porosity of tubular wall 115 is defined by a plurality of intersecting members 120 which define a first repeating pattern A and second repeating pattern B.

Figure 4:
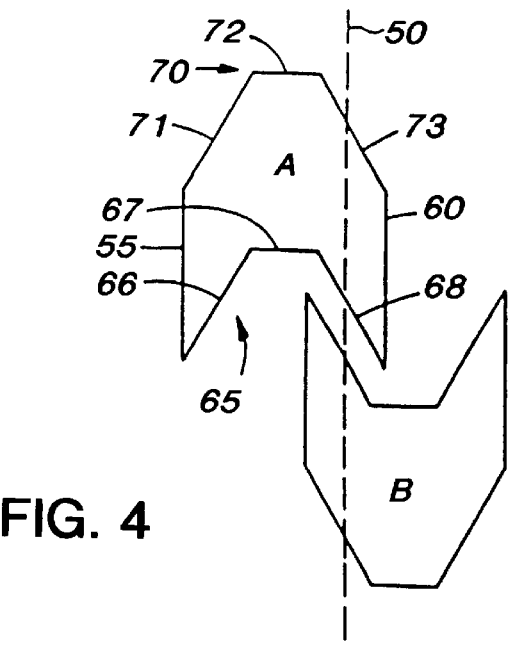
FIG. 4 illustrates an expanded two-dimensional representation of the repeating patterns present in the stents illustrated in FIGS. 1–3.

With reference to FIG. 4, there is illustrated an enlarged two-dimensional representation of first repeating pattern A and second repeating pattern B. These repeating patterns are illustrated with respect to a longitudinal axis 50 which is representative of the longitudinal axis which would be present in each of primary passageway 25, secondary passageways 30,35 and tubular wall 115 discussed above with reference to FIGS. 1, 2 and 3. As illustrated, repeating pattern A is a polygon comprising a pair of side walls 55,60. Side walls 55,60 are substantially parallel to longitudinal axis 50. Side walls 55,60 are connected by a concave-shaped wall 65 and a convex-shaped wall 70.

As illustrated, concave-shaped wall 65 is made up of a trio of segments 66,67,68. In the illustrated embodiment, segment 67 is the apex of concave-shaped wall 65. Convex-shaped wall 70 is made up of a trio of segments 71,72,73. In the illustrated embodiment, segment 72 is the apex of convex-shaped wall 70.

It will be appreciated by those of skill in the art that the provision of first repeating pattern A, as illustrated, necessarily defines and provides for second repeating pattern B. It will also be appreciated by those of skill in the art that second repeating pattern B is a mirror image of first repeating pattern A taken along an axis (not shown) substantially normal to longitude general axis 50.

It will be further appreciated by those of skill in the art that the shape of concave-shaped wall 65 and/or convex-shaped wall 70 can be modified without departing from the function and performance of the stent. For example, the trio of segments can be replaced by a suitably curved or arcuate wall. Alternatively, more than three segments can be used to define concave-shaped wall 65 and/or convex-shaped wall 70. Other modifications will be apparent to those of skill in the art.

It will be further appreciated by those of skill in the art that various walls of first repeating pattern A and second repeating pattern B may be omitted (and even desired) at selected points along the body of the stent without departing from the spirit and scope of the invention. For example, it is possible to omit one or both of side walls 55,60 at selected points along the body of the stent with a view to improving the longitudinal flexibility of the stent. Further, it is possible to omit one or more of segments 71,72,73 at selected points along the body of the stent with a view to improving the lateral flexibility of the stent.

With further reference to FIG. 2, it will be evident to those of skill in the art that intersection point 40 is an annular arrangement of second repeating pattern B which has been modified. Specifically, the modification is in two areas. First, a reinforcing bar 75 has been disposed between side walls 55,60 to connect segments 67 and 72. Second, a reinforcing segment 80 is provided midway between and has a similar shape to concave-shaped wall 65 and convex-shaped wall 70. These two areas of modification serve to reinforce intersection point 40. This facilitates alleviation of stresses under which this area of stent 10 is placed when it is expanded. It will of course be appreciated by those of skill in the art that modifications can be made to the design of intersection point 40 without departing from the spirit and scope of the invention. For example, the flexibility of stent 10 at intersection point 40 can be modified by judicious addition or omission of further reinforcing bars 75 and/or reinforcing segments 80.

Figure 5:
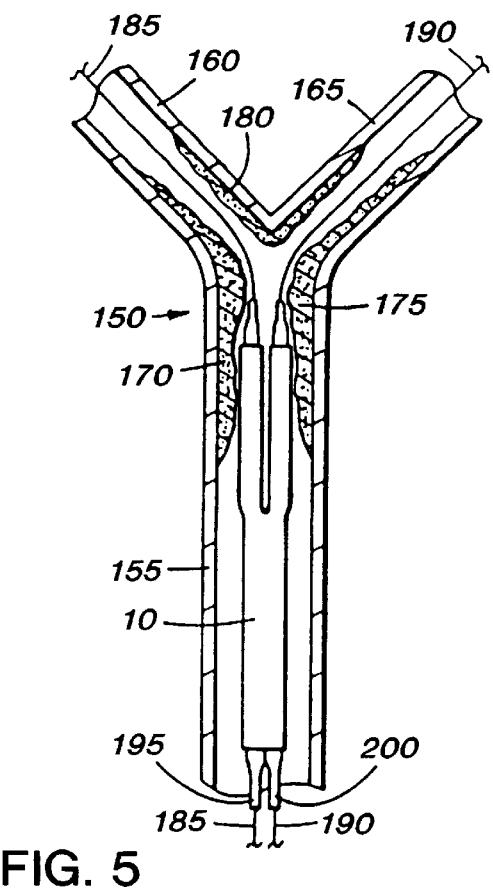
FIG. 5 illustrates a cross-section of a bifurcated body passageway into which the bifurcated stent of FIG. 1 is being delivered.
Figure 6:
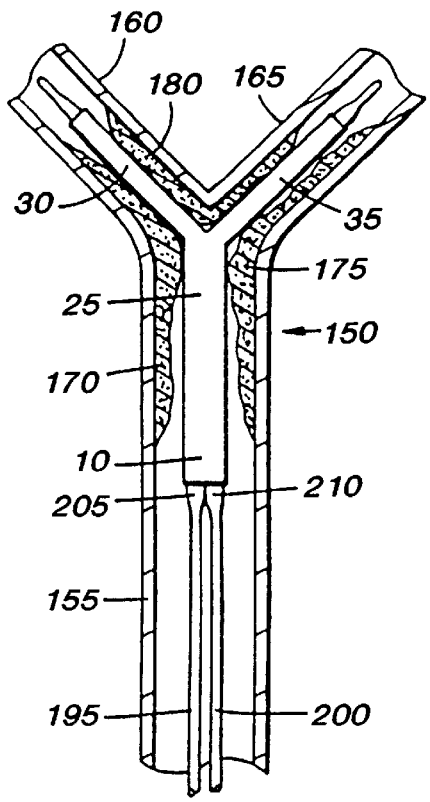
FIG. 6 illustrates a cross-section of a bifurcated body passageway in which the bifurcated stent of FIG. 1 is positioned in a first, contracted position.

With reference to FIGS. 5 and 6, there is illustrated a bifurcated body passageway 150 comprised of a proximal passageway 155 and a pair of distal passageways 160,165.

As illustrated, bifurcated body passageway 150 comprises a Type "D" Bifurcation lesion having characteristic blockages 170,175,180.

Stent 10 is delivered to bifurcated body passageway 150 in the following manner. Initially, a pair of guidewires 185,190 are inserted into proximal passageway 155 such that guidewire 185 enters distal passageway 160 and guidewire 190 enters distal passageway 165. The manner by which the guidewires are inserted is conventional and within the purview of a person skilled in the art.

As illustrated, stent 10 is positioned in association with a pair of catheters 195,200 (for clarity, the interior of stent 10 is not shown). Catheter 195 has associated with it a balloon 205. Catheter 200 has associated with it a balloon 210. Balloons 205,210 substantially fill primary passageway 25 of stent 10. Balloon 205 substantially fills secondary passageway 30 of stent 10. Balloon 210 substantially fills secondary passageway 35 of stent 10.

The stent/catheter/balloon combination is delivered through proximal passageway 155 with the aid of guidewires 185,190. As the stent/catheter/balloon combination approaches distal passageways 160,165, predisposition of guidewires 185,190 serves to separate secondary passageways 30,35 to be disposed in distal passageways 160,165, respectively. Thus, as illustrated in FIG. 6, stent 10 is positioned in place.

Figure 7:
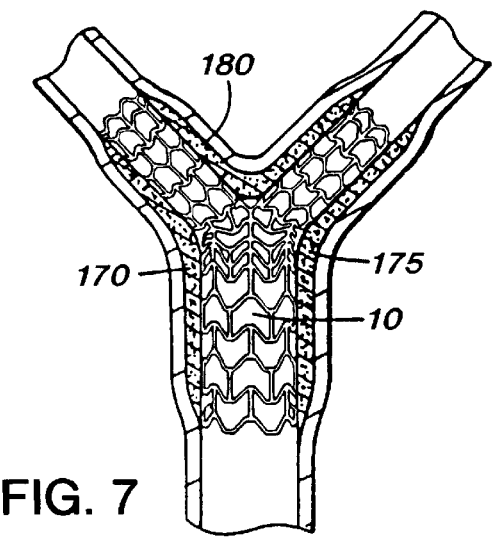
FIG. 7 illustrates a cross-section of a bifurcated body passageway in which the bifurcated stent of FIG. 1 positioned in a second, expanded position.

Once stent 10 is in position, balloons 205,210 are expanded resulting in implantation of stent 10 in the corresponding interior surfaces of proximal passageway 155 and distal passageways 160,165. Upon implantation of stent 10, balloons 205,210 are collapsed. Thereafter, catheters 195, 200 and guidewires 185,190 are removed leaving the implanted stent 10 shown in FIG. 7. As illustrated in FIG. 7, blockages 170,175,180 are bulged radially outwardly in combination with the appropriate portions of proximal passageway 155 and distal passageways 160,165 resulting in a reduction in the overall blockage in bifurcated body passage 150.

It will be apparent to those of skill in the art that implantation of stent 10 can be accomplished by various other means. For example, it is contemplated that it is possible to substitute the pair of catheter/balloon combinations illustrated in FIGS. 5 and 6 with a single, bifurcated catheter/balloon design which mimics the design of the stent. Thus, in this modification, the balloon and guidewire would be design to mimic the bifuracted designed of the stent. A further alternative, it is contemplated that the stent can be made of a suitable material which will expand when bifurcated body passageway 150 is flushed with a liquid having an elevated temperature (e.g. 150° F.–160° F.). Further, stent 10 can be designed to expand upon the application of mechanical forces other than those applied by a balloon/catheter. Still further, stent 10 can be designed as self-expanding to be implanted as described above. In this embodiment, the radially outward force exerted on the stent would be generated within the stent itself.

With regard to mono-tubular stent 100 depicted in FIG. 3, this stent can be implanted using a system similar to the one described above with reference to bifurcated stent 10 (FIGS. 5–7). In this instance, of course, a single guidewire, catheter and balloon can be used to position and expand the stent. Implantation of mono-tubular stents such as stent 100 is conventional and within the purview of a person skilled in the art. Further, mono-tubular stent 100 can be modified to provided localized reinforcement at certain points by judicious use of bars and segments similar to reinforcing bar 75 and reinforcing segment 80, respectively, used to reinforce intersection point 40 of stent 10 (FIG. 2).

Still further, the stent depicted in FIGS. 1–3 can be modified to omit, on a selected basis, first repeating pattern A and/or second repeating B with a view to improve the flexibility of the stent and to allow access to other structures (e.g. side branches/arteries) outside the bounds of the stent.

While this invention has been described with reference to illustrative embodiments, this description is not intended to be construed in a limiting sense. Various modifications of the illustrative embodiments, as well as other embodiments of the invention, will be apparent to persons skilled in the art upon reference to this description. It is therefore contemplated that the appended claims will cover any such modifications or embodiments.

What is claimed is:

1. An expandable bifurcated stent comprising a proximal end and a distal end in communication with one another, the proximal end comprising a primary passageway and the distal end comprising a pair of secondary passageways, the stent being expandable from a first, contracted position to a second, expanded position upon the application of a radially outward force exerted on the stent, the primary passageway and the pair of secondary passageways comprising a plurality of intersecting members which define a first repeating pattern, the pair of secondary passageways being connected to the primary passageway at an intersection region comprising a plurality of intersecting members which define a second repeating pattern different from the first repeating pattern, the second repeating pattern reinforcing the intersection region.

* * * * *